United States Patent
Luo et al.

(10) Patent No.: US 11,553,863 B2
(45) Date of Patent: Jan. 17, 2023

(54) VENOUS POSITIONING PROJECTOR

(71) Applicant: Industrial Technology Research Institute, Hsinchu (TW)

(72) Inventors: Shih-Bin Luo, Hsinchu County (TW); Chun-Chuan Lin, Hsinchu (TW); Wan-Ting Tien, Chiayi (TW); Hua-Ying Sheng, Hsinchu (TW); Hsiao-Yue Tsao, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 16/726,261

(22) Filed: Dec. 24, 2019

(65) Prior Publication Data
US 2021/0030345 A1 Feb. 4, 2021

Related U.S. Application Data

(60) Provisional application No. 62/881,372, filed on Aug. 1, 2019.

(30) Foreign Application Priority Data

Dec. 18, 2019 (TW) ................................ 108146405

(51) Int. Cl.
*A61B 5/15* (2006.01)
*G03B 21/20* (2006.01)
(Continued)

(52) U.S. Cl.
CPC ...... *A61B 5/150748* (2013.01); *A61B 5/0077* (2013.01); *A61B 5/489* (2013.01);
(Continued)

(58) Field of Classification Search
None
See application file for complete search history.

(56) References Cited

U.S. PATENT DOCUMENTS 4,967,264 A * 10/1990 Parulski ............... H04N 5/2259
348/456
5,969,754 A 10/1999 Zeman
(Continued)

FOREIGN PATENT DOCUMENTS

CN 101810482 3/2012
CN 203314943 12/2013
(Continued)

OTHER PUBLICATIONS

Manu Francis, et al., "A novel technique for forearm blood vein detection and enhancement." Biomedical Research, vol. 28, No. 7, Jan. 2017, pp. 2913-2919.
(Continued)

*Primary Examiner* — Rebecca A Volentine
(74) *Attorney, Agent, or Firm* — JCIPRNET

(57) ABSTRACT

A venous positioning projector includes an infrared light source module, a light splitting element, an infrared light image capture module, a processor, and a visible light projection module. The infrared light source module outputs a first infrared light to a target surface. The infrared light image capture module includes a filter and an infrared light image capture element. The light splitting element transmits a second infrared light reflected by the target surface to the filter. The infrared light image capture element receives the second infrared light passing through the filter. The processor generates venous image data according to the first infrared light and the second infrared light received by the infrared light image capture element. The visible light projection module generates a visible light based on the venous image data. The visible light is transmitted to the target surface through the light splitting element to generate a venous image.

7 Claims, 5 Drawing Sheets

(51) Int. Cl.
G02B 27/28 (2006.01)
A61B 5/00 (2006.01)
H04N 9/04 (2006.01)
H04N 5/235 (2006.01)

(52) U.S. Cl.
CPC ....... *G02B 27/283* (2013.01); *G03B 21/2033* (2013.01); *G03B 21/2066* (2013.01); *H04N 5/2354* (2013.01); *H04N 9/04553* (2018.08)

(56) References Cited

U.S. PATENT DOCUMENTS

| | | | |
|---|---|---|---|
| 8,078,263 | B2 | 12/2011 | Zeman et al. |
| 8,463,364 | B2 | 6/2013 | Wood et al. |
| 9,492,117 | B2 | 11/2016 | Goldman et al. |
| 9,789,267 | B2 | 10/2017 | Wood et al. |
| 10,357,200 | B2 | 7/2019 | Wood et al. |
| 2007/0158569 | A1* | 7/2007 | Zeman ............... A61B 5/489 250/330 |
| 2012/0259231 | A1* | 10/2012 | Tsubouchi ........... A61B 5/0071 600/477 |
| 2014/0039309 | A1* | 2/2014 | Harris .................. G16H 10/60 600/431 |
| 2014/0081247 | A1* | 3/2014 | Heiberger ............. A61F 9/008 606/4 |
| 2016/0262626 | A1* | 9/2016 | Pelosi ................. A61B 5/0077 |
| 2018/0288404 | A1* | 10/2018 | Ikehara ............... A61B 5/7445 |
| 2019/0216573 | A1* | 7/2019 | Nakamura ............ A61B 90/37 |
| 2019/0269485 | A1* | 9/2019 | Elbaz ................. A61B 1/00193 |
| 2020/0240840 | A1* | 7/2020 | Darty .................. G01J 3/0264 |
| 2021/0145536 | A1* | 5/2021 | Vayser ................. G01S 17/08 |

FOREIGN PATENT DOCUMENTS

| | | |
|---|---|---|
| CN | 102429644 | 4/2014 |
| CN | 104027072 | 2/2016 |
| CN | 205031338 | 2/2016 |
| CN | 106037674 | 10/2016 |
| EP | 1981395 | 6/2013 |
| EP | 3137138 | 1/2019 |
| TW | 200901939 | 1/2009 |
| TW | I481388 | 4/2015 |
| TW | I569830 | 2/2017 |
| TW | I664950 | 7/2019 |

OTHER PUBLICATIONS

Gunnar Lovhoiden, et al., "Clinical evaluation of vein contrast enhancement." Proceedings of SPIE, vol. 4615, May 13, 2002, pp. 61-70.

Gunnar Lovhoiden, et al., "Commercialization of vein contrast enhancement." Proceedings of SPIE, vol. 4958, Jul. 22, 2003, pp. 189-200.

Herbert D. Zeman, et al., "Design of a clinical vein contrast enhancing projector." Proceedings of SPIE, vol. 4254, Jun. 4, 2001, pp. 204-215.

Herbert D. Zeman, et al., "Enhancing the contrast of subcutaneous veins." Proceedings of SPIE, vol. 3595, Jul. 9, 1999, pp. 219-230.

Eli Peli, et al., "Image Enhancement for the Visually Impaired Simulations and Experimental Results." Investigative Ophthalmology & Visual Science, vol. 32, No. 8, Jul. 1991, pp. 2337-2350.

Nabila Bouzida, et al., "Near-infrared image formation and processing for the extraction of hand veins." Journal of Modern Optics, vol. 57, No. 18, Oct. 20, 2010, pp. 1731-1737.

Herbert D. Zeman, et al., "Optimization of subcutaneous vein contrast enhancement." Proceedings of SPIE, vol. 3911, May 3, 2000, pp. 50-57.

Herbert D. Zeman, et al., "Prototype vein contrast enhancer." Optical Engineering, vol. 44, No. 8, Aug. 1, 2005, pp. 1-9.

A. M. R. R. Bandara, et al., "Super-Efficient Spatially Adaptive Contrast Enhancement Algorithm for Superficial Vein Imaging." 2017 IEEE International Conference on Industrial and Information Systems, Dec. 15-16, 2017, pp. 1-7.

H. D. Zeman, et al., "The Clinical Evaluation of Vein Contrast Enhancement." Proceedings of the 26th Annual International Conference of the IEEE Engineering in Medicine and Biology Society, Sep. 1-5, 2004, pp. 1203-1206.

Sakshi Ranade, et al., "Vein Detection Using Infrared for Venepuncture." International Journal of Trend in Research and Development, vol. 4, No. 5, Sep.-Oct. 2017, pp. 12-15.

"Office Action of Taiwan Counterpart Application", dated Jun. 16, 2020, p. 1-p. 6.

* cited by examiner

VENOUS POSITIONING PROJECTOR

CROSS-REFERENCE TO RELATED APPLICATION

This application claims the priority benefits of U.S. provisional application Ser. No. 62/881,372, filed on Aug. 1, 2019, and Taiwan application serial no. 108146405, filed on Dec. 18, 2019. The entirety of each of the above-mentioned patent applications is hereby incorporated by reference herein and made a part of this specification.

BACKGROUND

Technical Field

The disclosure relates to a projector, and in particular, to a venous positioning projector.

Background

Subcutaneous vein interpretation may directly affect clinical puncture and subsequent drug administration effects. In clinical practice, the blood vessels of infants or obese or dark-skinned subjects are more difficult to be interpreted, leading to increased difficulty in venipunctures. In addition to causing pain to the subjects, an unsuccessful venipuncture may cause complications such as bruises, bacterial infections, phlebitis, thrombosis, embolism, or nerve damage. Therefore, the development of a device or a method that can improve a success rate of a first venipuncture injection is a well-being for both the subjects and medical staff.

SUMMARY

Embodiments of the disclosure provide a venous positioning projector, which helps improve a success rate of a first venipuncture injection.

According to the embodiments of the disclosure, the venous positioning projector includes an infrared light source module, a light splitting element, an infrared light image capture module, a processor, and a visible light projection module. The infrared light source module is configured to output a first infrared light to a target surface. The light splitting element is disposed on a transmitting path of a second infrared light reflected by the target surface. The infrared light image capture module includes a filter and an infrared light image capture element. The second infrared light transmitted to the light splitting element is transmitted to the filter through the light splitting element. The filter allows the second infrared light to pass through. The infrared light image capture element is disposed on the transmitting path of the second infrared light passing through the filter and receives the second infrared light. The processor is coupled to the infrared light source module and the infrared light image capture element, wherein the processor generates venous image data according to the first infrared light and the second infrared light. The visible light projection module is coupled to the processor and generates a visible light based on the venous image data. The light splitting element is further disposed on a transmitting path of the visible light, and the visible light is transmitted to the target surface through the light splitting element to generate a venous image. The infrared light image capture module and the visible light projection module share an optical axis between the light splitting element and the target surface.

In order to make the aforementioned and other objectives and advantages of the disclosure comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1:
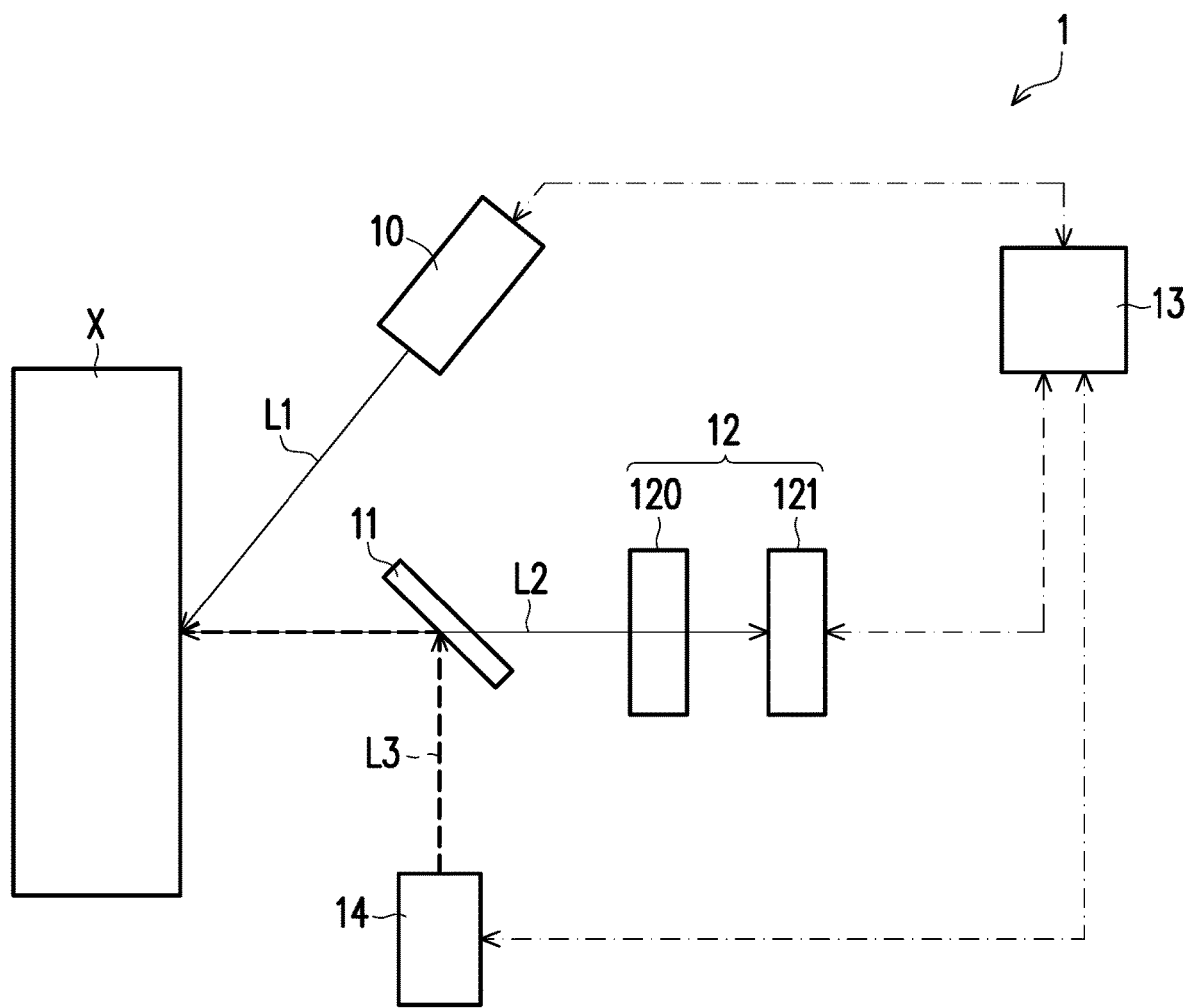
FIG. 1 is a schematic view of a venous positioning projector according to a first embodiment of the disclosure.

The directional terms mentioned in implementations, such as "above", "below", "front", "back", "left", and "right", refer only to the directions in the appended drawings. Therefore, the directional terms are used for illustration instead of limiting the disclosure.

In the appended drawings, each drawing illustrates the common features of the method, structure, or material used in a particular exemplary embodiment. However, these drawings should not be interpreted as defining or limiting the scope or nature of these exemplary embodiments. For example, for clarity, the relative size, thickness, and position of each film, region, or structure may be reduced or enlarged.

In the implementations, the same or similar elements have the same or similar reference numerals and the details thereof are omitted. In addition, features in different exemplary embodiments may be combined with each other without conflict, and simple equivalent changes and modifications made in accordance with this specification or claims shall remain within the scope of the patent.

Terms such as "first" and "second" mentioned in this specification or claims are used only to name discrete elements or to distinguish different embodiments or scopes, and are not used to limit the upper or lower limits on the quantity of elements, nor to define an order in which the elements are made or disposed. Furthermore, an element/film disposed at (or above) another element/film may include the existence or absence of an additional element/film between two elements/films; in other words, the element/film may be disposed directly or indirectly at (or above) the other element/film. In addition, that one element/film is directly disposed on (or above) another element/film indicates that the two elements/films are in contact with each other and that no additional element/film exists between the two elements/films.

FIG. 1 is a schematic view of a venous positioning projector 1 according to a first embodiment of the disclosure, and illustrates that vein positioning and projection are performed on a target surface X by using the venous positioning projector 1. The target surface X is, for example, a surface of a subject and on which subcutaneous vein interpretation or venipuncture is to be performed. The subject may be human beings or other animals.

Referring to FIG. 1, the venous positioning projector 1 includes an infrared light source module 10, a light splitting element 11, an infrared light image capture module 12, a processor 13, and a visible light projection module 14.

The infrared light source module 10 is configured to output a first infrared light L1 to the target surface X. In the present embodiment, a quantity of infrared light source modules 10 included by the venous positioning projector 1 is one, and a central wavelength of the first infrared light L1 is, for example, 850±5 nm or 940±5 nm. However, the quantity of infrared light source modules 10 included by the venous positioning projector 1 and the central wavelength of the first infrared light L1 are changeable according to requirements, which is not limited herein.

The infrared light source module 10 may include at least one infrared light-emitting diode or at least one infrared light laser (for example, an infrared light laser diode, which is not limited herein) that is configured to provide the first infrared light L1. In an embodiment, the infrared light source module 10 adopts one or more infrared light-emitting diodes, and the first infrared light L1 is an infrared light with light type divergence and energy divergence. Due to low costs and relatively divergent light type and energy of an infrared light-emitting diode, the infrared light source module 10 adopting one or more infrared light-emitting diodes may reduce costs of the venous positioning projector 1 and damage caused to eyes by inadvertent radiation of the first infrared light L1. In another embodiment, the infrared light source module 10 adopts one or more infrared light lasers, and the first infrared light L1 is an infrared light with a relatively collimated light type and concentrated energy. Due to a relatively collimated light type and concentrated energy of the infrared light laser, if the infrared light source module 10 adopts one or more infrared light lasers, an operation distance between the venous positioning projector 1 and the target surface X is not easily limited by the infrared light source module 10.

Under the radiation of the first infrared light L1, a part of the first infrared light L1 is absorbed by the target surface X (or the hemoglobin or other tissue beneath it), and a part of the first infrared light L1 is reflected by the target surface X. For ease of description, the part of the first infrared light L1 reflected by the target surface X is referred to as a second infrared light L2 below.

The light splitting element 11 is disposed on a transmitting path of the second infrared light L2 reflected by the target surface X. The light splitting element 11 is adapted to transmit the second infrared light L2 reflected by the target surface X to the infrared light image capture module 12. For example, the light splitting element 11 may be a polarization light splitting element or a dichroic element. When the light splitting element 11 is a polarization light splitting element, the light splitting element 11 may split a light according to a polarization state of the light. For example, the light splitting element 11 may allow an S-polarization light (a light with a polarization state perpendicular to a paper surface) to pass through and reflect a P-polarization light (a light with a polarization state parallel to the paper surface); or the light splitting element 11 may allow the P-polarization light to pass through and reflect the S-polarization light. When the light splitting element 11 is a dichroic element, the light splitting element 11 may split a light according to a wavelength of the light. For example, the light splitting element 11 may allow an infrared light to pass through and reflect a visible light; or the light splitting element 11 may allow a visible light to pass through and reflect an infrared light.

In an architecture of FIG. 1, the light splitting element 11 may allow the infrared light (for example, the second infrared light L2) to pass through and reflect a visible light L3. In another embodiment, the infrared light image capture module 12 and the visible light projection module 14 may exchange positions. In this case, the light splitting element 11 may allow the visible light L3 to pass through and reflect the infrared light (for example, the second infrared light L2).

In the present embodiment, the light splitting element 11 is of a plate shape. However, in another embodiment, the light splitting element 11 may be of a prism shape. In other words, the light splitting element 11 may be composed of a plate and an optical film formed thereon, or composed of a prism and an optical film formed thereon.

In the present embodiment, the light splitting element 11 is located outside the transmitting path of the first infrared light L1. In other words, the light splitting element 11 is not located on the transmitting path of the first infrared light L1, that is, the first infrared light L1 is not transmitted to the target surface X through the light splitting element 11. However, in another embodiment, the light splitting element 11 may be located on the transmitting path of the first infrared light L1, and the first infrared light L1 may be transmitted to the target surface X through the light splitting element 11.

The infrared light image capture module 12 is located on the transmitting path of the second infrared light L2 from the light splitting element 11. The infrared light image capture module 12 may include a filter 120 and an infrared light image capture element 121. However, element composition of the infrared light image capture module 12 is changeable according to requirements, which is not limited herein. For example, the infrared light image capture module 12 may further include a lens assembly (not shown). The lens assembly may be disposed between the filter 120 and the light splitting element 11, and the lens assembly may include at least one lens.

The second infrared light L2 transmitted to the light splitting element 11 is transmitted to the filter 120 through the light splitting element 11. In the present embodiment, the filter 120 is disposed on the transmitting path of the second infrared light L2 passing through the light splitting element 11. In another embodiment, the filter 120 is disposed on the transmitting path of the second infrared light L2 reflected by the light splitting element 11. The filter 120 allows the second infrared light L2 to pass through. For example, the filter 120 allows at least part of the second infrared light L2 to pass through and filters light in other wave bands, to reduce interference caused by the light in other wave bands.

The infrared light image capture element 121 is disposed on the transmitting path of the second infrared light L2 passing through the filter 120 and receives the second infrared light L2. For example, the infrared light image capture element 121 may include a charge coupled device (CCD) or a complementary metal oxide semiconductor (CMOS), which is not limited herein.

The processor 13 is coupled to the infrared light source module 10 and the infrared light image capture element 121. The coupling may include transmission of a signal in a wired or wireless manner. The processor 13 may generate venous image data according to the first infrared light L1 output by the infrared light source module 10 and the second infrared light L2 received by the infrared light image capture element 121. Specifically, hemoglobin in a subject has higher absorption of near-infrared light than other tissues. A body part of the subject to be interpreted or injected is exposed to the infrared light (the first infrared light L1) to enable the hemoglobin in the blood to absorb a part of the infrared light, and then an absorption rate of a specific wavelength is calculated according to an amount of the reflected infrared light (the second infrared light L2) and the venous blood, to reconstruct venous image data (including data such as positions and sizes of blood vessels) corresponding to the target surface X.

The visible light projection module 14 is coupled to the processor 13 and generates the visible light L3 based on the venous image data. For example, the visible light projection module 14 may include a laser projection module. The laser projection module may include a red laser, a green laser, and a blue laser outputting a red light, a green light, and a blue light respectively. A wavelength of the red light falls within a range of 632 nm to 642 nm, that is, 632 nm≤the wavelength of the red light≤642 nm. A wavelength of the green light falls within a range of 515 nm to 530 nm, that is, 515 nm≤the wavelength of the green light≤530 nm. A wavelength of the blue light falls within a range of 440 nm to 460 nm, that is, 440 nm≤the wavelength of the blue light≤460 nm. However, types of the visible light projection module 14, element composition of the laser projection module, types of color lights, and wavelength ranges of all color lights are changeable according to requirements, which is not limited herein.

In an embodiment, the visible light projection module 14 may use a laser scan projection module to perform projection imaging on a blood vessel (for example, a vein). The laser scan projection module has features of high brightness, high contrast, wide color gamut, low power consumption and no focus. Therefore, adopting the laser scan projection module may enable the operation distance between the venous positioning projector 1 and the target surface X not to be limited by the visible light projection module 14.

The light splitting element 11 is further disposed on a transmitting path of the visible light L3, and the visible light L3 is transmitted to the target surface X through the light splitting element 11 to generate a venous image (not shown). Specifically, the infrared light image capture module 12 and the visible light projection module 14 are designed to share an optical axis between the light splitting element 11 and the target surface X, to avoid image distortion caused by oblique projection or oblique image capture, so that the venous image projected to the target surface X has the same size and position as a real vein, making it convenient for medical staff to check the distribution and direction of blood vessels, thereby improving a success rate of first venipuncture injection.

In the present embodiment, the processor 13 may calculate the first infrared light L1 and the second infrared light L2 in real time and output corresponding signals to the visible light projection module 14, so that the venous image is projected onto the target surface X in real time. The venous image is also updated in real time once the venous positioning projector 1 and the target surface X generate relative displacement. Therefore, an error rate of venipuncture caused by displacement of the venous positioning projector 1 or the target surface X can be reduced.

Figure 2:
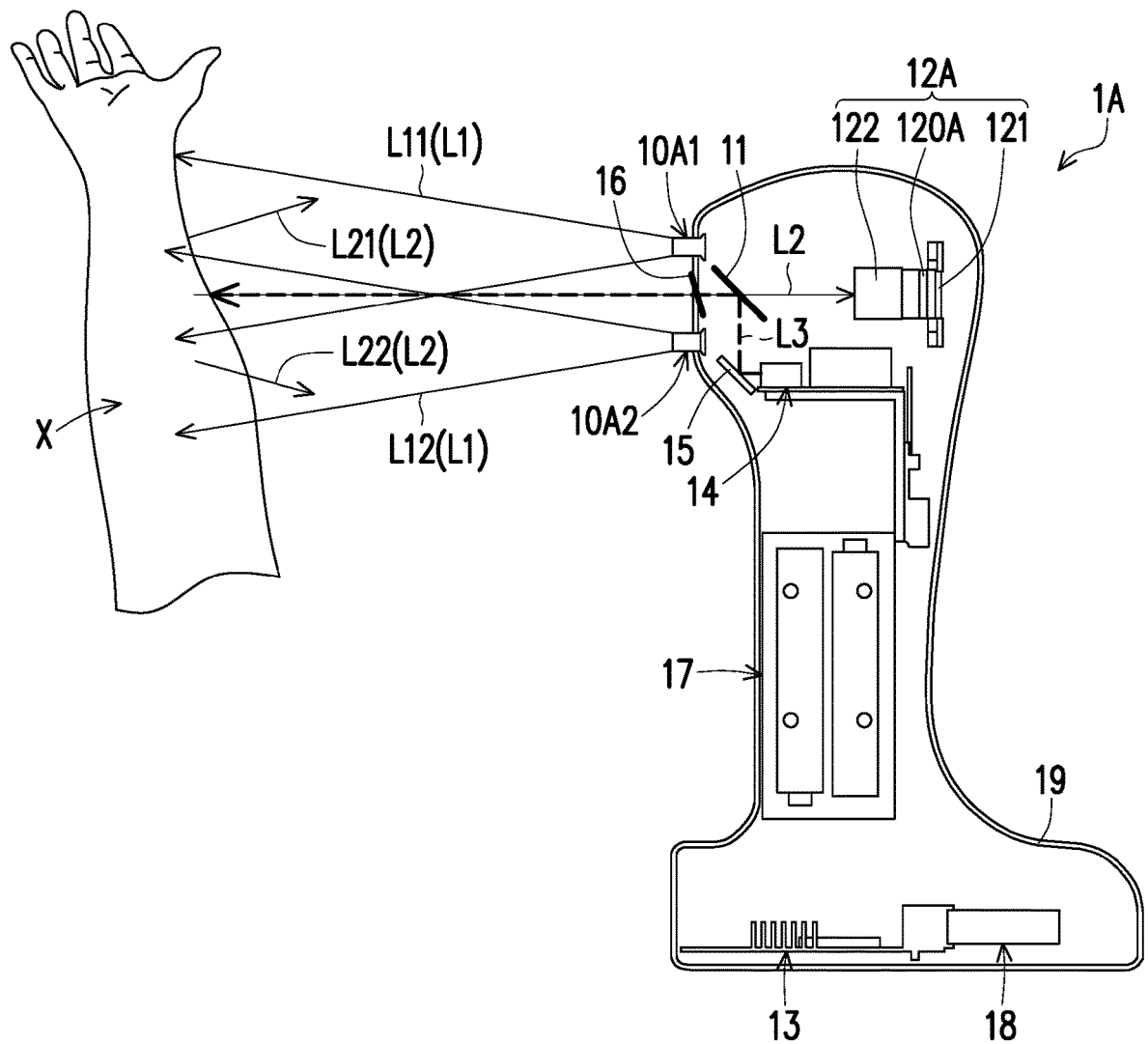
FIG. 2 is a schematic view of a venous positioning projector according to a second embodiment of the disclosure.
Figure 3:
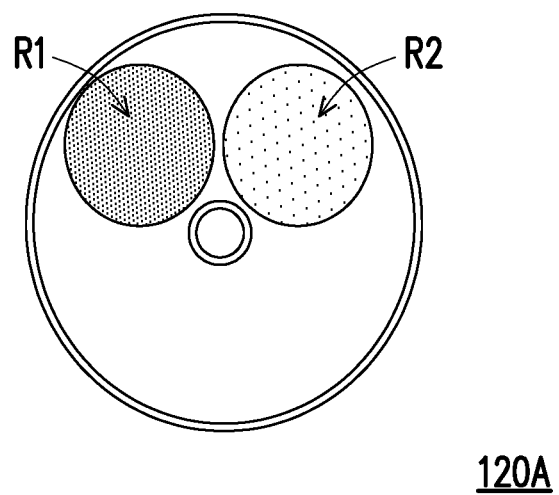
FIG. 3 is a schematic front view of a filter in FIG. 2.
Figure 4:
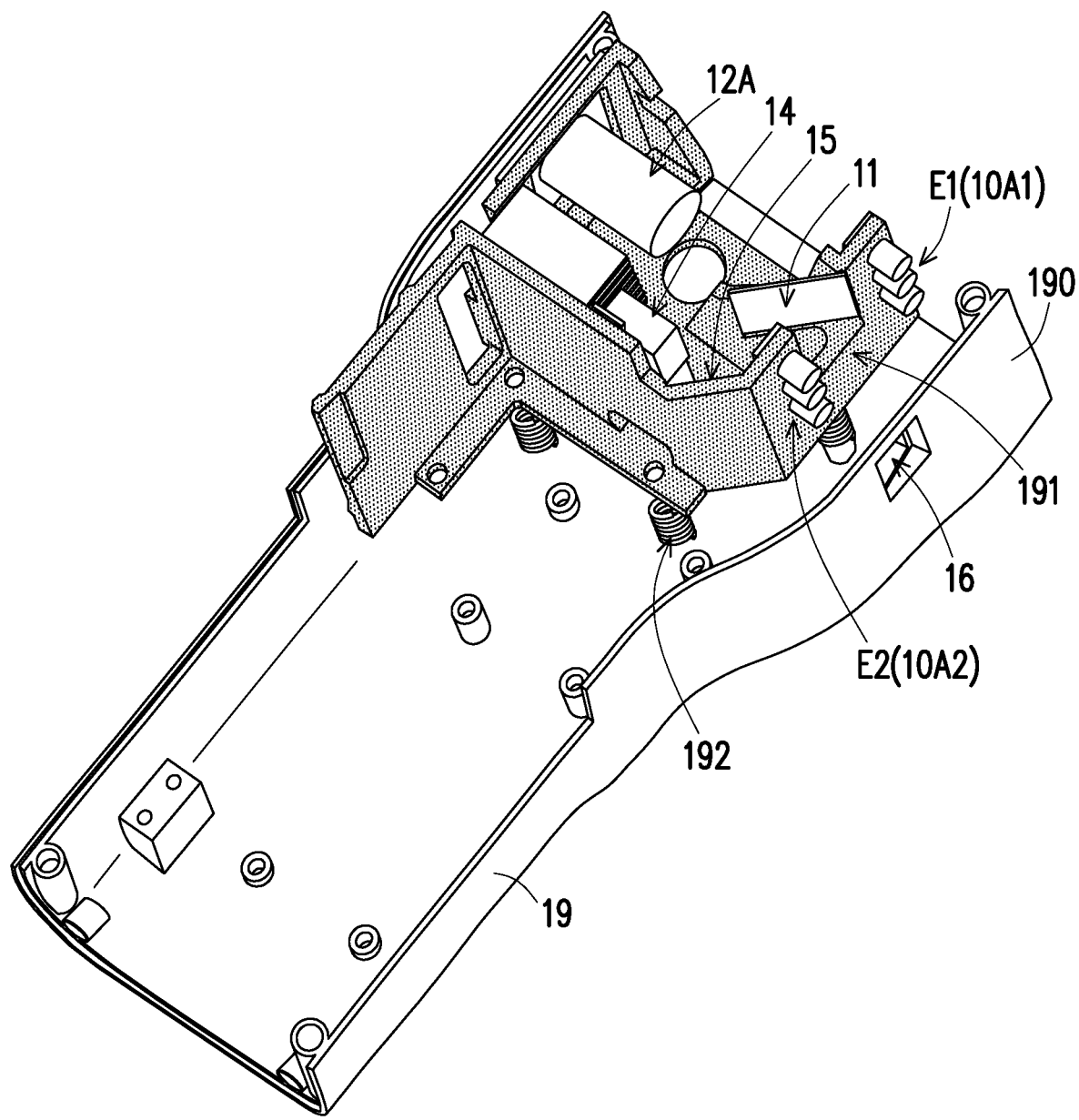
FIG. 4 is a schematic partial three-dimensional view of the venous positioning projector in FIG. 2.

FIG. 2 is a schematic view of a venous positioning projector 1A according to a second embodiment of the disclosure, and illustrates that vein positioning and projection are performed on a target surface X by using the venous positioning projector 1A. FIG. 3 is a schematic front view of a filter 120A in FIG. 2. FIG. 4 is a schematic partial three-dimensional view of the venous positioning projector 1A in FIG. 2.

Referring to FIG. 2, the venous positioning projector 1A is similar to the venous positioning projector 1 in FIG. 1. However, it should be noted that the venous positioning projector 1A includes two infrared light source modules (for example, an infrared light source module 10A1 and an infrared light source module 10A2), a light splitting element 11, an infrared light image capture module 12A, a processor 13, a visible light projection module 14, a reflection element 15, a transparent protection element 16, a power module 17, a sensor module 18, and a housing 19.

The infrared light source module 10A1 and the infrared light source module 10A2 are embedded in an outer layer of the housing 19 and respectively located on opposite sides (for example, an upper side and a lower side) of the transparent protection element 16. The infrared light source module 10A1 and the infrared light source module 10A2 may each include at least one light-emitting element. The at least one light-emitting element may be an infrared light-emitting diode or an infrared light laser. An infrared light output by the light-emitting element of the infrared light source module 10A1 and an infrared light output by the light-emitting element of the infrared light source module 10A2 may have same or different central wavelengths.

In the present embodiment, the infrared light source module 10A1 includes at least one first light-emitting element E1 (three first light-emitting elements E1 are shown in FIG. 4). The infrared light source module 10A2 includes at least one second light-emitting element E2 (three second light-emitting elements E2 are shown in FIG. 4). The first infrared light L1 includes a first light L11 output by the three first light-emitting elements E1 and a second light L12 output by the three second light-emitting elements E2. The first light L11 and the second light L12 have different central wavelengths. For example, the central wavelengths of the first light L11 and the second light L12 are 850±5 nm and 940±5 nm respectively. A longer wavelength indicates a stronger capability of the infrared light to penetrate skin, that is, infrared lights with different central wavelengths can capture different depths. Therefore, an effect of venous detection and positioning may be improved by setting light-emitting elements with infrared lights with different central wavelengths.

The three first light-emitting elements E1 and the three second light-emitting elements E2 are turned on in a first time period and a second time period respectively. For example, the three first light-emitting elements E1 are turned on in the first time period and the three second light-emitting elements E2 are turned off in the first time period. Therefore, the venous positioning projector 1A provides the first light L11 in the first time period. The three second light-emitting elements E2 are turned on in the second time period and the three first light-emitting elements E1 are turned off in the second time period. Therefore, the venous positioning projector 1A provides the second light L12 in the second time period.

The target surface X absorbs a part of the first light L11 in the first time period, and reflects a part of the first light L11, where the part of the first light L11 reflected by the target surface X in the first time period is referred as a third light L21 below. Similarly, the target surface X absorbs a part of the second light L12 in the second time period, and reflects a part of the second light L12, where the part of the second light L12 reflected by the target surface X in the second time period is referred as a fourth light L22 below.

That is, the second infrared light L2 includes the third light L21 and the fourth light L22 reflected by the target surface X in the first time period and the second time period respectively, and central wavelengths of the third light L21 and the fourth light L22 are 850±5 nm and 940±5 nm respectively.

Referring to FIG. 2 and FIG. 3, the filter 120A includes a first filter region R1 and a second filter region R2. The first filter region R1 allows the third light L21 to pass through and filters the fourth light L22. The second filter region R2 allows the fourth light L22 to pass through and filters the third light L21. For example, the filter 120A may be a circular carrier on which a filter layer is formed, and the filter 120A is adapted to rotate along its central axis, so that the first filter region R1 cuts into a transmitting path of the third light L21 in the first time period, and the second filter region R2 cuts into a transmitting path of the fourth light L22 in the second time period.

In the present embodiment, in addition to the filter 120A and the infrared light image capture element 121, the infrared light image capture module 12A may further include a lens assembly 122. The lens assembly 122 may be disposed between the filter 120A and the light splitting element 11, and the lens assembly 122 may include at least one lens.

The reflection element 15 is disposed on the transmitting path of the visible light L3, and the visible light L3 is transmitted to the light splitting element 11 through the reflection element 15. Specifically, the reflection element 15 is configured to redirect a light transmitting path of the visible light L3, to reduce a volume or longitudinal dimension of the venous positioning projector 1A. For example, the reflection element 15 may include a mirror, a prism, or any other element suitable for redirecting the light transmitting path.

In the present embodiment, the reflection element 15 is located outside the transmitting path of the first infrared light L1. In other words, the reflection element 15 is not located on the transmitting path of the first infrared light L1, that is, the first infrared light L1 is not transmitted to the target surface X through the reflection element 15. However, in another embodiment, the reflection element 15 may be located on the transmitting path of the first infrared light L1, and the first infrared light L1 may be transmitted to the target surface X through the reflection element 15.

The transparent protection element 16 is disposed at a light entry of the housing 19 and is located between the light splitting element 11 and the target surface X. The second infrared light L2 passes through the transparent protection element 16 to the housing 19 and then to the light splitting element 11, and finally is transmitted to the infrared light image capture module 12A. The transparent protection element 16 may be a transparent substrate with a metal oxide layer (for example, indium tin oxide) formed on its surface to achieve an antistatic or anti-electromagnetic wave effect, which is not limited herein.

The power module 17 is disposed in the housing 19 and is electrically connected to the infrared light source module 10A1, the infrared light source module 10A2, the infrared light image capture module 12A, the processor 13, the visible light projection module 14, and the sensor module 18, to provide necessary power for these elements to work. For example, the power module 17 may include one or more batteries.

The sensor module 18 senses an orientation (for example, an oblique direction or an oblique angle) of the venous positioning projector 1A. For example, the sensor module 18 may include a gyroscope, an acceleration sensor, other sensor devices, or a combination of at least two of the foregoing sensor devices. The sensor module 18 is coupled to the processor 13, and the processor 13 may control on and off of the infrared light source module (for example, the infrared light source module 10A1 and the infrared light source module 10A2) based on a sensing result of the sensor module 18. For example, when sensing that the oblique angle of the venous positioning projector 1A is greater than a preset angle (for example, an angle such as 30 degrees at which an infrared light may enter the human eye), the sensor module 18 may control light output energy of the infrared light source module to approach zero, and when sensing that the oblique angle of the venous positioning projector 1A is less than the preset angle, the sensor module 18 may control the light output energy of the infrared light source module to return to normal. The on and off of the first infrared light L1 is controlled in real time by following the orientation of the venous positioning projector 1A, to avoid damage caused to eyes by inadvertent radiation of the first infrared light L1, thereby achieving a function of protecting the eyes. In an embodiment, the processor 13 may be a central processing unit (CPU), and the processor may control on and off of the infrared light source module by using a controller coupled between the processor 13 and the infrared light source module. In another embodiment, the sensor module 18 may control on and off functions of the infrared light source module by combining with the processor 13, for example, a mercury switch, which is not limited herein.

The housing 19 is configured to secure the infrared light source module 10A1, the infrared light source module 10A2, the light splitting element 11, the infrared light image capture module 12A, the processor 13, the visible light projection module 14, the reflection element 15, the transparent protection element 16, the power module 17, and the sensor module 18. In an embodiment, the housing 19 may be designed in favor of a handheld system for ease of use. In an embodiment, as shown in FIG. 4, the housing 19 may include a body 190, configured to secure the infrared light source module 10A1, the infrared light source module 10A2, the light splitting element 11, the infrared light image capture module 12A, a common light path mechanism 191 of the reflection element 15 and the visible light projection module 14, and a plurality of shock absorption elements 192. The shock absorption element 192 may be disposed between the body 190 and the common light path mechanism 191 to achieve an effect of shock absorption. For example, the shock absorption element 192 may include a spring, a shock absorption cotton, or other suitable shock absorption elements. In an embodiment, the body 190 may be a transparent body, a non-transparent body, or a combination thereof. In an embodiment, the body 190 may be a metal housing for ease of heat dissipation.

Figure 5:
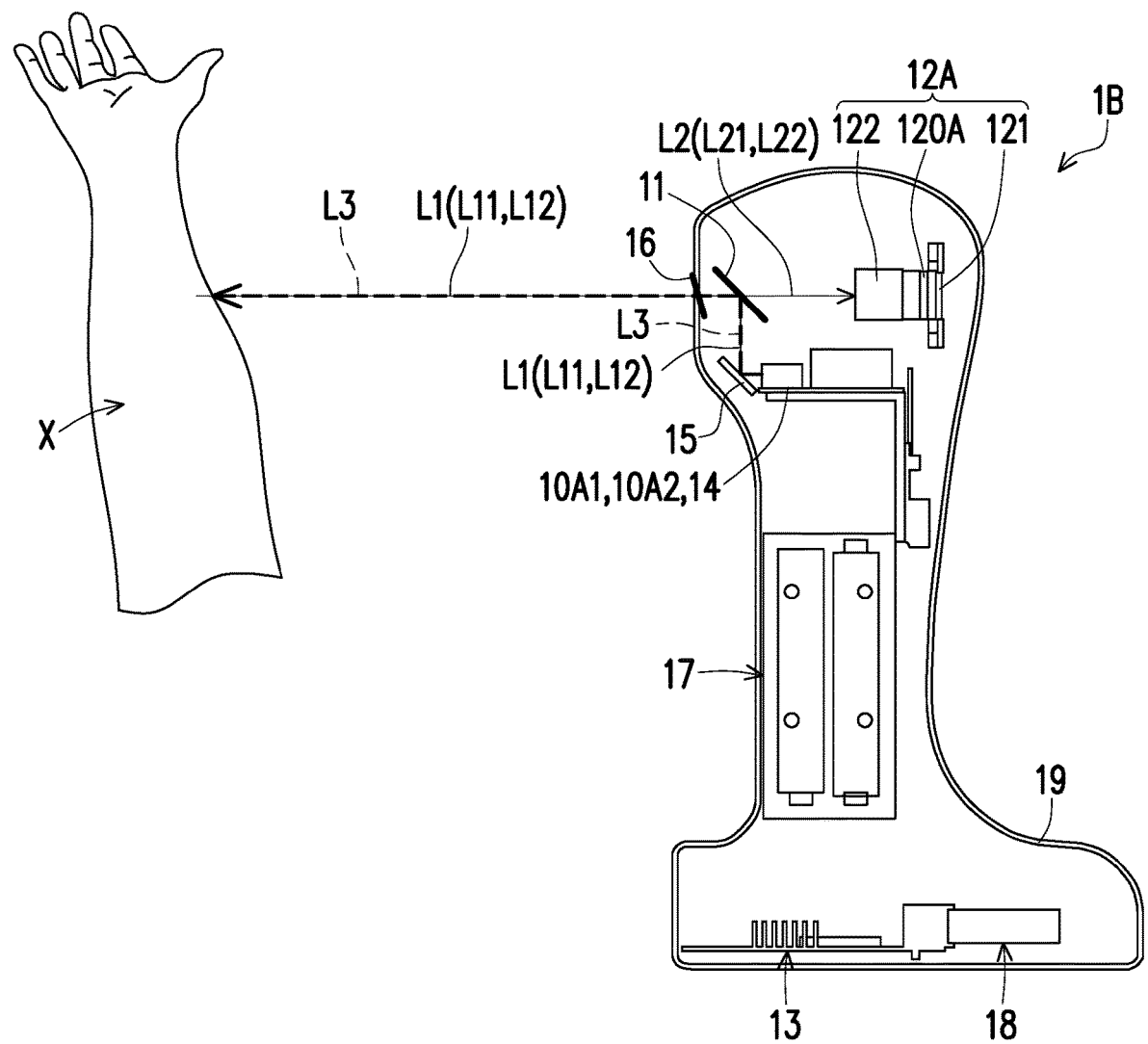
FIG. 5 is a schematic view of a venous positioning projector according to a third embodiment of the disclosure.

FIG. 5 is a schematic view of a venous positioning projector 1B according to a third embodiment of the disclosure, and illustrates that vein positioning and projection are performed on a target surface X by using the venous positioning projector 1B.

Referring to FIG. 5, the venous positioning projector 1B is similar to the venous positioning projector 1A in FIG. 2. However, it should be noted that, in the venous positioning projector 1B, the infrared light source module (for example, an infrared light source module 10A1 and an infrared light source module 10A2) and a visible light projection module 14 are integrated into a laser projection module, where a first infrared light L1 output by the infrared light source module and a visible light L3 output by the visible light projection module 14 are both laser lights, and the first infrared light L1 and the visible light L3 are projected onto the target surface X in different time periods along a same transmitting path. That is, because the infrared light source module and the visible light projection module 14 are integrated into the laser projection module, the first infrared light L1 output by the infrared light source module and the visible light L3 output by the visible light projection module 14 have a common light path to the target surface X.

Specifically, a reflection element 15 is disposed on the transmitting path of the first infrared light L1 and the visible light L3, and the first infrared light L1 and the visible light L3 are transmitted to a light splitting element 11 through the reflection element 15. The light splitting element 11 is further disposed on the transmitting path of the first infrared light L1, and the first infrared light L1 is transmitted to the target surface X through the light splitting element 11. Furthermore, the first infrared light L1 (or the visible light L3) is, for example, sequentially reflected by the reflection element 15, reflected by the light splitting element 11, and projected onto the target surface X by passing through a transparent protection element 16.

In the present embodiment, the light splitting element 11 reflects the first infrared light L1 and the visible light L3, and allows the second infrared light L2 to pass through. For example, the light splitting element 11 may be a polarization light splitting element, for example, a wire-grid polarizing beam splitter, which is not limited herein. Correspondingly, the first infrared light L1 and the visible light L3 may be linearly polarized laser lights, for example, an S-polarization laser light or a P-polarization laser light. The second infrared light L2 reflected by the target surface X is a non-polarization laser light (that is, the second infrared light L2 includes an S-polarization laser light and a P-polarization laser light). Only one of the S-polarization laser light and the P-polarization laser light in the second infrared light L2 transmitted to the light splitting element 11 can pass through the light splitting element 11 and be transmitted to the infrared light image capture module 12A.

For example, the light splitting element 11 is a polarization light splitting element that allows the S-polarization light to pass through and reflects the P-polarization light. Correspondingly, the first infrared light L1 and the visible light L3 may be P-polarization laser lights. Only the S-polarization laser light in the second infrared light L2 transmitted to the light splitting element 11 can pass through the light splitting element 11 and be transmitted to the infrared light image capture module 12A. In addition, if the light splitting element 11 may be a polarization light splitting element that allows the P-polarization light to pass through and reflects the S-polarization light, the first infrared light L1 and the visible light L3 may be S-polarization laser lights. Only the P-polarization laser light in the second infrared light L2 transmitted to the light splitting element 11 can pass through the light splitting element 11 and be transmitted to the infrared light image capture module 12A.

In the present embodiment, the first infrared light L1 includes a first light L11 and a second light L12, and the second infrared light L2 includes a third light L21 and a fourth light L22, where a central wavelength of the first light L11 (or the third light L21) is different from a central wavelength of the second light L12 (or the fourth light L22). In other words, the infrared light source module in the venous positioning projector 1B includes a plurality of light-emitting elements outputting infrared lights with different central wavelengths. Correspondingly, the venous positioning projector 1B may adopt a filter 120A shown in FIG. 3. In another embodiment, the infrared light source module in the venous positioning projector 1B may include one or more light-emitting elements outputting an infrared light with a single central wavelength. Correspondingly, the venous positioning projector 1B may adopt a filter capable of filtering a light in a wave band other than the infrared light to reduce noise.

Based on the above, in the venous positioning projector in the disclosure, the infrared light is used to detect a subcutaneous superficial vein, a peak absorption of a specific wavelength is calculated by using the venous blood, and a venous image is projected in real time onto a target surface by the visible light projection module through photoelectric information conversion, making it convenient for medical staff to check the distribution and direction of blood vessels, thereby improving a success rate of first venipuncture injection.

In an embodiment, the visible light projection module may use a laser scan projection module to perform projection imaging on a blood vessel (for example, a vein). The laser scan projection module has features of high brightness, high contrast, wide color gamut, low power consumption and no focus. Therefore, adopting the laser scan projection module may enable an operation distance between the venous positioning projector and the target surface not to be limited by the visible light projection module. In an embodiment, the infrared light source module may be provided with light-emitting elements with infrared lights with different central wavelengths, to improve an effect of venous detection and positioning. In an embodiment, an effect of antistatic or anti-electromagnetic wave may be achieved by disposing the transparent protection element. In an embodiment, a function of protecting eyes may be achieved by disposing the sensor module. In an embodiment, the housing may be disposed to secure elements in the venous positioning projector. In an embodiment, the housing may be designed in favor of a handheld system for ease of use. In an embodiment, the housing may include a plurality of shock absorption elements, to achieve an effect of shock absorption.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A venous positioning projector, comprising:
an infrared light source module, configured to output a first infrared light to a target surface;
a light splitting element, disposed on a transmitting path of a second infrared light reflected by the target surface;
an infrared light image capture module, comprising a filter and an infrared light image capture element, wherein the second infrared light transmitted to the light splitting element is transmitted to the filter through the light splitting element, the filter allows the second infrared light to pass through, and the infrared light image capture element is disposed on the transmitting path of the second infrared light passing through the filter and receives the second infrared light;
a processor, coupled to the infrared light source module and the infrared light image capture element, wherein the processor generates venous image data according to the first infrared light and the second infrared light;
a visible light projection module, coupled to the processor and generating a visible light based on the venous image data, wherein the light splitting element is further disposed on a transmitting path of the visible light, and the visible light is transmitted to the target surface through the light splitting element to generate a venous image, wherein the infrared light image capture module and the visible light projection module share an optical axis between the light splitting element and the target surface, the infrared light source module comprises at least one first light-emitting element and at least one second light-emitting element, the at least one first light-emitting element and the at least one second light-emitting element are disposed on opposite sides of the optical axis, the first infrared light comprises a first light output by the at least one first light-emitting element and a second light output by the second light-emitting element, the first light and the second light have different central wavelengths, the at least one first light-emitting element and the at least one second light-emitting element are turned on in a first time period and a second time period, respectively, the second infrared light comprises a third light and a fourth light that are reflected by the target surface in the first time period and the second time period, respectively, the filter comprises a first filter region and a second filter region, the first filter region allows the third light to pass through and filters the fourth light, the second filter region allows the fourth light to pass through and filters the third light, the first filter region cuts into a transmitting path of the third light in the first time period, and the second filter region cuts into a transmitting path of the fourth light in the second time period, the first time period and the second time period are mutually exclusive, wherein the filter rotates about a central axis to switch between different filter regions on the same optical path; and a transparent protection element, disposed between the light splitting element and the target surface, wherein the transparent protection element is a transparent substrate with a metal oxide layer.

2. The venous positioning projector according to claim 1, wherein the light splitting element is located outside a transmitting path of the first infrared light, and the light splitting element is a polarization light splitting element or a dichroic element.

3. The venous positioning projector according to claim 1, wherein the infrared light source module comprises at least one infrared light-emitting diode.

4. The venous positioning projector according to claim 1, wherein a central wavelength of the first infrared light is 850±5 nm or 940±5 nm.

5. The venous positioning projector according to claim 1, wherein central wavelengths of the first light and the third light are 850±5 nm, and central wavelengths of the second light and the fourth light are 940±5 nm.

6. The venous positioning projector according to claim 1, further comprising:
a reflection element, disposed on the transmitting path of the visible light and located outside a transmitting path of the first infrared light, wherein the visible light is transmitted to the light splitting element through the reflection element.

7. The venous positioning projector according to claim 1, further comprising:
a sensor module, sensing an orientation of the venous positioning projector, wherein the sensor module is coupled to the processor, and the processor controls on and off of the infrared light source module based on a sensing result of the sensor module.

* * * * *